US012110479B2

(12) United States Patent
Tay et al.

(10) Patent No.: US 12,110,479 B2
(45) Date of Patent: Oct. 8, 2024

(54) MICROFLUIDIC DEVICES, SYSTEMS, AND METHODS FOR INVESTIGATING THREE-DIMENSIONAL CELLULAR STRUCTURES

(71) Applicant: THE UNIVERSITY OF CHICAGO, Chicago, IL (US)

(72) Inventors: Savas Tay, Chicago, IL (US); Michael Junkin, Chicago, IL (US); Brooke Schuster, Naperville, IL (US)

(73) Assignee: THE UNIVERSITY OF CHICAGO, Chicago, IL (US)

( * ) Notice: Subject to any disclaimer, the term of this patent is extended or adjusted under 35 U.S.C. 154(b) by 1171 days.

(21) Appl. No.: 16/438,356

(22) Filed: Jun. 11, 2019

(65) Prior Publication Data

US 2019/0376013 A1 Dec. 12, 2019

Related U.S. Application Data

(60) Provisional application No. 62/683,161, filed on Jun. 11, 2018.

(51) Int. Cl.
*C12M 3/06* (2006.01)
*C12M 1/00* (2006.01)
(Continued)

(52) U.S. Cl.
CPC ............ *C12M 23/16* (2013.01); *C12M 23/22* (2013.01); *C12M 29/00* (2013.01); *C12N 5/0693* (2013.01);
(Continued)

(58) Field of Classification Search
None
See application file for complete search history.

(56) References Cited

U.S. PATENT DOCUMENTS

| 2007/0264705 A1* | 11/2007 | Dodgson | ............... C12M 23/12 435/283.1 |
| 2009/0093374 A1* | 4/2009 | Suh | ....................... C12M 25/02 506/10 |

(Continued)

FOREIGN PATENT DOCUMENTS

CN 105396633 A * 3/2016

OTHER PUBLICATIONS

Wu et al. Development of PDMS microbioreactor with well-defined and homogenous culture environment for chondrocyte 3-D culture. Biomed Microdevices (2006) 8:331-340 (Year: 2006).*

(Continued)

*Primary Examiner* — William H. Beisner
(74) *Attorney, Agent, or Firm* — Norton Rose Fulbright US LLP (57) ABSTRACT

This disclosure includes microfluidic devices, systems, and methods for investigating three-dimensional (3D) cell structures (e.g., organoids, spheroids, scaffolds, hydrogels, and the like). Some examples of the present microfluidic devices comprise: a body having a first end, a second end, to lateral edges, an upper side, a lower side, a first layer region between a medial plane of the body and the lower side, and a second layer region between the medial plane and the upper side. In some such examples, the first layer region defines one or more rows of wells, with each well open at the medial plane and having a bottom between the medial plane and the lower side. In some such examples, the second layer region can defines one or more elongated channels open at the medial plane and having a top between the medial plane and the upper side, with each of the elongated channels aligned with one of the rows of wells such that the respective elongated channel is in fluid communication with each of the wells in the respective row of wells.

12 Claims, 8 Drawing Sheets

(51) Int. Cl.
*C12N 5/09* (2010.01)
*G01N 33/50* (2006.01)
(52) U.S. Cl.
CPC ...... *G01N 33/5011* (2013.01); *C12N 2513/00* (2013.01)

(56) References Cited

U.S. PATENT DOCUMENTS

| | | | | |
|---|---|---|---|---|
| 2009/0305397 | A1* | 12/2009 | Dodgson | C12M 23/24 435/307.1 |
| 2011/0183312 | A1* | 7/2011 | Huang | C12M 23/16 435/286.5 |
| 2012/0135446 | A1* | 5/2012 | Collins | C12M 23/16 435/29 |
| 2014/0248698 | A1* | 9/2014 | Kotera | C12N 5/0606 435/366 |
| 2018/0327701 | A1* | 11/2018 | Fernandez Ledesma | B01L 3/5027 |

OTHER PUBLICATIONS

Occhetta et al. "High-Throughput Microfluidic Platform for 3D Cultures of Mesenchymal Stem Cells", Chapter 23, Zuzana Koledova (ed.), 3D Cell Culture: Methods and Protocols, Methods in Molecular Biology, vol. 1612, 2017, pp. 303-323 (Year: 2017).*
Fang et al., "Three-Dimensional Cell Cultures in Drug Discovery and Development" *SLAS Discov.* 2017, 22 (5), 456-472.
Griffith et al., "Capturing complex 3D tissue physiology in vitro" *Nat Rev Mol Cell Biol* 2006, 7 (3), 211-224.
Heltberg et al., "Noise Induces Hopping between NF-KB Entrainment Modes" *Cell Syst.* 2016, 3 (6), 532-539.
Hutchinson et al., "High drug attrition rates—where are we going wrong?" *Nat Rev Clin Oncol* 2011, 8 (4), 189-190.
Junkin et al., "High-Content Quantification of Single-Cell Immune Dynamics" *Cell Rep.* 2016, 15 (2), 411-422.
Kellogg et al., "Noise Facilitates Transcriptional Control under Dynamic Inputs" *Cell* 2015, 160 (3), 381-392.
Pampaloni et al., "The third dimension bridges the gap between cell culture and live tissue" *Nat Rev Mol Cell Biol* 2007, 8 (10), 839-845.
Zhang et al., "Universal microfluidic system for control and analysis of cell dynamics" *Cell* 2017, 48 pages.

* cited by examiner

MICROFLUIDIC DEVICES, SYSTEMS, AND METHODS FOR INVESTIGATING THREE-DIMENSIONAL CELLULAR STRUCTURES

CROSS-REFERENCE TO RELATED APPLICATIONS

The present application claims the benefit of U.S. Provisional Application No. 62/683,161 filed on Jun. 11, 2018, the entire content of which is incorporated herein by reference.

FIELD OF INVENTION

The present invention relates generally to investigating three-dimensional (3D) cell structures (e.g., organoids, spheroids, scaffolds, or other 3D cell structures, such as in a scaffold or hydrogel-like environment); and more particularly, but not by way of limitation, to microfluidic devices, systems, and methods for investigating such 3D cell structures.

BACKGROUND

Drug-attrition rates for cancer are much higher than in other therapeutic areas [4] and, as a result, there is an ongoing need to find optimal strategies to evaluate novel and effective agents and develop curative chemotherapies. One tool for doing so would be appropriate tumor models that can physiologically replicate the key features of human tissue. Historically, two-dimensional (2D) cancer cell lines with limited representation of the actual tumors from which they are derived have been utilized for cancer and drug-development research, as well as expensive and time-consuming patient-derived xenograft models or mutation-based rodent models.

Classically, cancer cell biology research and drug development have relied on in vitro monolayer human tumor-derived cell lines and in vivo xenograft mice; however, previous clinical application has revealed that reliance on these models may be limiting [5]. Because 2D cell lines lack a three-dimensional (3D) structure that could recapitulate the shape and structure of the tumor, 2D cell models may impact the behavior of the cells and the response to drug treatment. PDX are useful in that they have a 3D structure, but require a large section of tumor (typically ~100 mm$^3$) to expand in the mouse. Also, the establishment of PDX tumors can take up to 6 months, or longer, limiting patient benefit.

3D ex vivo models can overcome many of the deficiencies of prior 2D and PDX models. 3D models can not only better replicate natural tissue mechanical stresses, but also provide a more-representative pathophysiological condition than the classic monolayer cultures; they can also be established in a shorter period and much more economically than patient-derived xenograft (PDX) model [6]. Additionally, cancer diagnosis often involves collection of a biopsy, such as an endoscopic ultrasound-guided fine-needle aspiration (FNA).

Unlike many other culture systems, organoids may be cultured from a single needle aspiration with a high success rate. The potential to use patient-derived organoids for therapeutic screening can have significant clinical benefits. Organoids open the possibility of deep genomic characterization and ex vivo therapeutic testing in patients that have traditionally been understudied in research settings. Once established, organoid cultures can be cryopreserved and expanded, genotyped, and challenged with approved standard-of-care and/or off-label therapies within weeks. Thus, patient-derived cancer organoids show great promise for enabling organoid-guided second line therapeutic options to be offered to the patient. A summary of the advantages and disadvantages of the three different models can be found in Table 1.

TABLE 1

Comparison of 2D, PDX, and organoid models for cancer investigations

|  | 2D monolayers | PDX | Organoids |
|---|---|---|---|
| Advantage | Rapid expansion | 3D architecture<br>Stroma<br>Vascular system | 3D architecture<br>Small amount of primary tumor (FNA) needed<br>Less costly<br>Rapid expansion |
| Disadvantage | Lack of 3D architecture<br>Unclear if culture conditions select for asubset of tumor cells | Rapid experimental interrogation is difficult<br>Time consuming and costly<br>Large primary tumor pieceis needed<br>Interspecies differences<br>Murine stroma<br>Immuno-compromised mice limits the use of PDX to study immunotherapy | Only epithelial cells |

However, in spite of the potential advantages of organoids, there are significant limitations to their widespread utilization. First, relatively little histopathological characterization of organoids has been reported, and the significance of the organoid morphologies remains unclear. Also, a deep genetic characterization of human-derived organoids cultures is needed, to determine whether they represent the genetic heterogeneity and therapeutic sensitivity profile of the entire primary tumor. Second, it remains to be seen how often organoids are predictive of tumor response in patients. Such research could also be sped up considerably if a standardized culturing device and set of protocols were broadly available to the vast community of laboratories studying cancer biology and therapeutic development. Third, even with more-broadly available culturing protocols and dissemination of know-how, the speed and cost of culturing and comprehensive screening of organoids for drug sensitivities is prohibitive due to expensive reagents like Matrigel® and the labor-intensive nature of screens. Most laboratories that are equipped for large scale screening rely on plate-based screening that can cost tens of thousands of dollars per screen.

SUMMARY

This disclosure includes embodiments of: microfluidic devices, systems, and methods, for example that are well-suited for investigating 3D cellular structures (e.g., organoids, spheroids, scaffolds, or other 3D cell structures, such as in a scaffold or hydrogel-like environment). For example, the present microfluidic devices, systems, and methods can—relative to prior approaches for culturing organoids—be lower-cost, higher-throughput, and more-broadly applicable to both research and clinical settings. At least some of the present systems and methods are especially suited for probing changes involved at each stage in tumorigenesis. At least some of the present microfluidic devices, systems, and methods can overcome many of the above-described organoid limitations with standardized, miniaturized assays that can be performed in a highly-reproducible environment using relatively small amounts of reagents and an automated system that can culture and screen thousands of conditions (e.g., with relatively minimal training and investment).

Additionally, while cancer diagnosis often involves collection of a biopsy (e.g., endoscopic, ultrasound-guided FNA), organoids can often be cultured from a single needle aspiration with a high success rate. This ability to harvest samples less invasively makes the present devices, systems, and methods well-suited for investing characteristics and changes involved at each stage in tumorigenesis by enabling detailed, parallel analysis on samples that can be harvested more-frequently, and by permitting therapeutic screening of organoids derived from patients themselves rather than mouse or other models. Organoids and other 3D cell structures can also be used to study other diseases, and drug therapies for other diseases, such as cystic fibrosis.

The present devices can include of an array of wells and channels passing over respective subsets of the wells such that each channel can direct fluids to and/or away from a corresponding subset of the wells. Each well can serve as a culture chamber for growing cells (e.g., organoids), for example, in a growth medium such as an extracellular three-dimensional environment (e.g., gelatinous protein, Matrigel®, hydrogels, and/or the like).

Certain embodiments of the present microfluidic devices can be configured to automate high-throughput creation, culture, stimulation, assaying, and/or harvesting of organoids or other 3D cell structures under dynamic conditions. Certain embodiments of the present microfluidic devices can also provide robust investigations and data, for example through multiple parallel investigations of a subject organoid type. For example, certain configurations of the present systems include a controller and microfluidic multiplexer (which may, for example, be included in a single device housing), such that culture conditions in the wells may be altered and/or maintained by a control program, such as an automated control program. Such a control program(s) can be configured to selectively guide or direct fluids to and/or away from individual subsets of the wells to create individual experimental conditions in each such subset. The stimulations supplied to organoids may include specific profiles of culture conditions (e.g., growth medium, drug stimulation, staining, and/or the like) that may predetermined when programming an experiment and/or adjusted during an experiment (e.g., in response to developments during the experiments).

These levels of automation permit programming and application of any number of dynamic conditions, and overcomes certain limitations of manual pipetting such as limited complexity, higher error rates, and extended time scales required for manual pipetting. In at least some of the present automated embodiments, organoids may be cultured and stimulated while being simultaneously imaged in three dimensions, for example via phase-contrast and fluorescence deconvolution microscopy, to provide real-time measurements of cell reactions, movements, and proliferation. In certain embodiments of the present systems, the structure of the microfluidic device allows the upper fluidic supply channels to be removed to expose the cell-containing gel for facile harvesting of organoids or cells after completion of an experiment for subsequent analysis (e.g., sequencing, expansion, and/or the like).

The following non-limiting Examples 1-9 include exemplary configurations of (and features, variations, and combinations thereof in) the present microfluidic devices (e.g., for investigating three-dimensional (3D) cell structures).

Example 1

The present devices can comprise: a body having a first end, a second end, two lateral edges, an upper side, a lower side, a first layer region between a medial plane of the body and the lower side, and a second layer region between the medial plane and the upper side; where the first layer region defines one or more rows of wells, each well open at the medial plane and having a bottom between the medial plane and the lower side; and where the second layer region defines one or more elongated channels open at the medial plane and having a top between the medial plane and the upper side, each of the elongated channels aligned with one of the rows of wells such that the respective elongated channel is in fluid communication with each of the wells in the respective row of wells.

Example 2

In the microfluidic device of Example 1, the body defines a plurality of rows of wells and a plurality of elongated channels, which can permit parallel processing of channels, each plurality of wells.

Example 3

In the microfluidic device of any of Examples 1-2, the first layer region is defined by a first material layer having a first surface and a second surface, and the second layer region is defined by a second material layer having a first surface and a second surface; and: the second surface of the first material layer defines the lower side of the body; the first surface of the second material layer defines the upper side of the body; and the first surface of the first material layer contacts the second surface of the second material layer along the medial plane. Having the layer regions defined by independent layers facilitates loading of wells, assembly and disassembly of the body, and removal of samples from the wells.

Example 4

In the microfluidic device of any of Examples 1-3, the body comprises polydimethylsiloxane (PDMS).

Example 5

In the microfluidic device of any of Examples 1-4, the first layer region and/or first material layer is coupled to a first glass slide, which can offer support for the first material layer and the body overall.

Example 6

In the microfluidic device of Example 5, a portion of the first layer region between the first glass side and a bottom of the well(s) is transparent, which can permit imaging of contents of the well(s) while the device is in an assembled state.

Example 7

In the microfluidic device of any of Examples 1-6, the device further comprises: a frame; where the body is clamped to the frame with the lower side of the body closer to the frame than is the upper side of the body; and where the frame is configured to permit imaging of the wells through the lower side of the body.

Example 8

In the microfluidic device of any of Examples 1-7, where the body defines one or more inlet channels and one or more outlet channels, each inlet channel extending through an exterior surface of the body to a first end of a respective one of the elongated channel(s), and each outlet channel extending from a second end of a respective one of the elongated channel(s) through the exterior surface of the body. Such inlet channels permit fluids to be delivered to the well(s) corresponding to each elongated channel while the body is in an assembled state, and such inlet channels permit fluids to be evacuated from the well(s) corresponding to each elongated channel while the body is in an assembled state.

Example 9

In the microfluidic device of Example 8, the inlet channels and outlet channels extend through the top side of the body, which can facilitate access to the inlet and outlet channels when the device is in an assembled state (e.g., with the frame of Example 7).

The following non-limiting Examples 10-12 include exemplary configurations of (and features, variations, and combinations thereof in) the present microfluidic systems (e.g., for investigating three-dimensional (3D) cell structures).

Example 10

The present systems can comprise: a microfluidic device (e.g., of any of Examples 1-9); and a multiplexer having a plurality of multiplexer inlets, one or more multiplexer outlets, one or more waste inlets, and a plurality of valves selectively permitting fluid communication between respective multiplexer inlets and multiplexer outlet(s), each of the multiplexer outlet(s) and the waste inlet(s) in communication with at least one of the elongated channel(s) of the body of the microfluidic device. The combination of the multiplexer with the microfluidic device can facilitate precise control of delivery and removal of fluids and/or reagents to the well(s). In some instances, The combination of the multiplexer and the microfluidic device can also facilitate mixing of fluids and/or reagents prior to delivery to the well(s), followed by seamless delivery of the mixed fluids and/or reagents.

Example 11

In the microfluidic system of Example 10, the system further comprises: a controller coupled to the microfluidic multiplexer and configured to send signals to selectively open or close the valves to direct flow between respective multiplexer inlets and multiplexer outlet(s). The combination of the controllers, multiplexer, and microfluidic device can facilitate automated processing of samples and experiments, including for example, mixing, delivery, removal of fluids and/or reagents to/from the well(s).

Example 12

In the microfluidic system of Example 11, the body defines a plurality of rows of wells and a plurality of elongated channels, and the multiplexer and controller are configured to deliver different fluid compositions to different channels and their respective wells. The combination of the controllers, multiplexer, and microfluidic device with multiple elongated channels and rows of wells can facilitate parallel, automated processing of multiple samples and multiple experiments, including for example, mixing, delivery, removal of fluids and/or reagents to/from the well(s).

The following non-limiting Examples 13-20 include exemplary configurations of (and features, variations, and combinations thereof in) the present methods (e.g., for investigating three-dimensional (3D) cell structures).

Example 13

The present methods can comprise: exposing cells to culture medium in a well of a first material layer, the first material layer having a lower side and an upper side through which the well is open; coupling a second material layer to the first material layer such that a lower side of the second material layer faces the upper side of the first material layer, an elongated channel open through the lower side of the second material layer, and the second material layer is coupled to the first material layer such that the well is substantially sealed except for being in fluid communication with the channel; and directing fluid to the well of the first material layer via the channel of the second material layer.

Example 14

In the method of Example 13, the first material layer defines a plurality of rows of wells open through the upper side, the second material layer defines a plurality of elongated channels open through the lower side of the second material layer, and the second material layer is coupled to the first material layer such that the wells in each of the rows are substantially sealed except for being in fluid communication with a respective one of the channels; and directing fluid to the well comprises directly fluid to a plurality of the wells by directing fluid to at least two of the channels. Directing fluid to at least two channels can facilitate processing of an increased number of samples or processing of multiple parallel experimental protocols.

Example 15

In the method of Example 14, different fluid compositions are directed to different channels and their respective wells.

Example 16

In the method of any of Examples 11-14, the method further comprises: permitting the cells to grow in the well into a 3D cellular structure, optionally an organoid. Permitting the growth of the cells can facilitate the study of the cells during the growth phase and after the cells have developed into the 3D cellular structure or organoid.

Example 17

In the method of Example 13, the fluid comprises a drug, which can facilitate the investigation of the interaction of the drug with the particular 3D cellular structure (e.g., cancer or healthy cells of a particular organ).

Example 18

In the method of any of Examples 13-17, a portion of the first material layer between the bottom side and a bottom of the well(s) is transparent.

Example 19

In the method of any of Examples 13-18, the method further comprises: imaging at least a portion of the cells through the lower side of the first material layer; and optionally, delivering a contrast agent to the at least one well(s) of the first material layer via the respective channel(s) of the second material layer.

Example 20

In the method of any of Examples 13-17, the cells comprise cancer cells.

The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the term "substantially" may be substituted with "within [a percentage] of" what is specified, where the percentage includes 0.1, 1, 5, and 10 percent.

The terms "comprise" and any form thereof such as "comprises" and "comprising," "have" and any form thereof such as "has" and "having," and "include" and any form thereof such as "includes" and "including" are open-ended linking verbs. As a result, an apparatus that "comprises," "has," or "includes" one or more elements possesses those one or more elements, but is not limited to possessing only those elements. Likewise, a method that "comprises," "has," or "includes" one or more steps possesses those one or more steps, but is not limited to possessing only those one or more steps.

Any embodiment of any of the apparatuses, systems, and methods can consist of or consist essentially of—rather than comprise/include/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

Further, a device or system that is configured in a certain way is configured in at least that way, but it can also be configured in other ways than those specifically described.

The feature or features of one embodiment may be applied to other embodiments, even though not described or illustrated, unless expressly prohibited by this disclosure or the nature of the embodiments.

Some details associated with the embodiments described above and others are described below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers. Views in the figures are drawn to scale, unless otherwise noted, meaning the sizes of the depicted elements are accurate relative to each other for at least the example in the view.

DETAILED DESCRIPTION OF ILLUSTRATIVE EMBODIMENTS

The present devices and systems can provide robust and streamlined automated microfluidic investigations under dynamic conditions. Broadly, the present devices can include an array of wells that each serve as a culture chamber for organoids, for example grown inside Matrigel® or hydrogels. In automated configurations of the present systems, the culture conditions of the wells can be created and/or maintained by an automated control program guiding fluidic supply to well subsets (e.g., rows) to create individual experimental conditions in each subset (e.g., row of wells). Conditions can be varied by supplying different fluid compositions to the wells via channels passing over the wells (and over the organoids residing in the wells). Stimulations supplied to organoids can follow specific profiles of culture conditions (e.g., medium, drug stimulation, and/or staining) that may be predetermined when programming an experiment and/or varied manually by a user during an experiment (e.g., responsive to variations or developments arising during the experiment). This level of automation [1], [2], [3] can allow relatively easy programming and application of any number of dynamic conditions, and can overcome certain limits of manual pipetting that may otherwise limit complexity, increase errors, and increase the time required to perform investigations or experiments. In at least some configurations of the present microfluidic devices, organoids or other 3D cellular structures in the wells may be imaged in 3D, such as via phase contrast and fluorescence deconvolution microscopy, to provide real-time measurements of cell reactions, movements, and proliferation while they are being cultured and/or stimulated. Once an experiment is complete, at least some configurations of the present microfluidic devices permit an upper layer with the supply channels to be removed to expose the cell-containing gel and thereby permit harvesting of organoids for subsequent analysis (e.g., sequencing, expansion, and/or the like).

I. Examples of Structures & Manufacture of the Present Microfluidic Devices

Figures 1A, 1B, 1C:
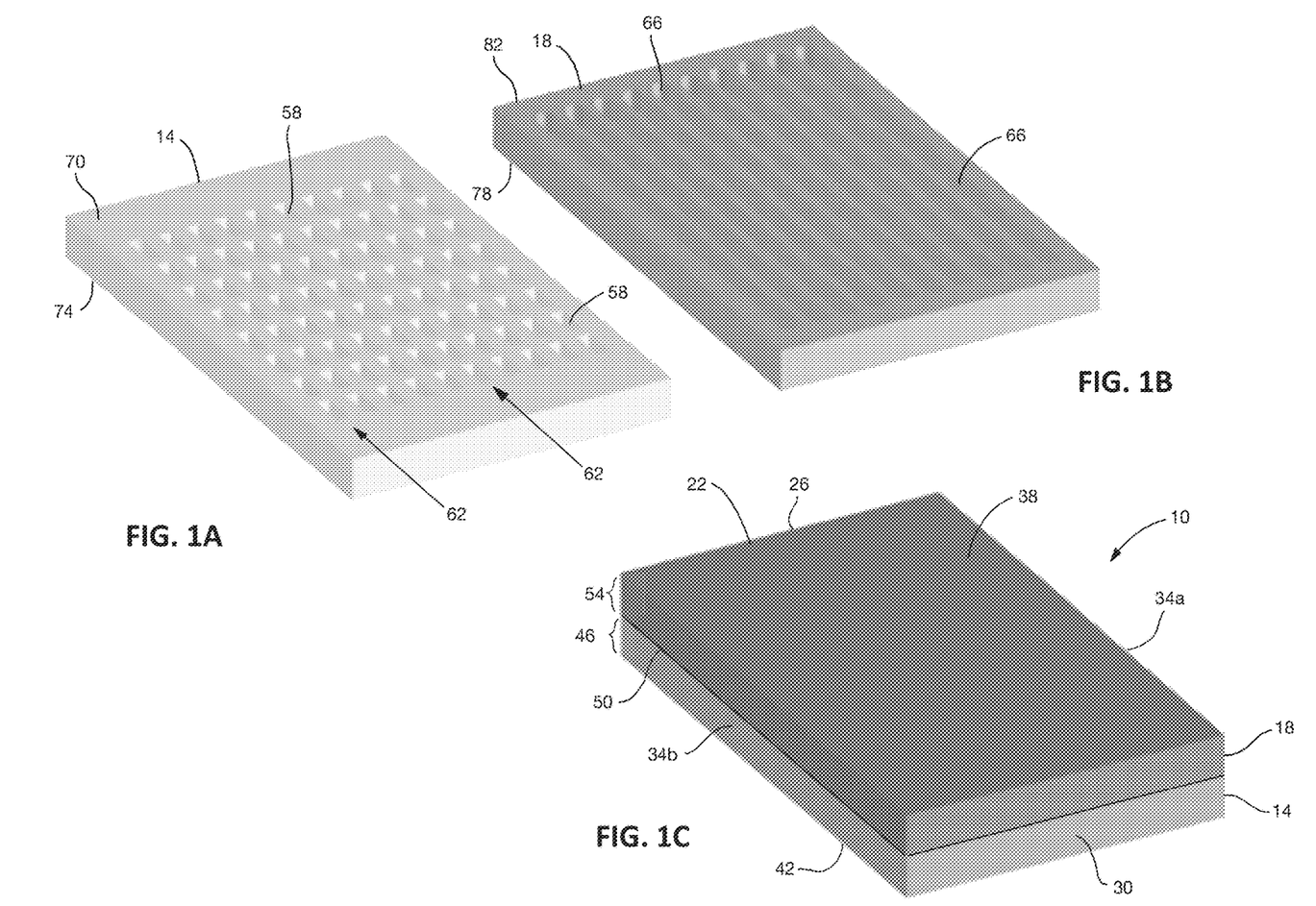
FIGS. 1A and 1B depict lower and upper layers, respectively, of one example of the present microfluidic devices.
FIG. 1C depicts the upper and lower layers of the device of FIGS. 1A and 1B in an assembled configuration.

Referring now to the drawings, and more particularly to FIGS. 1A-1C, shown there is an example 10 of the present microfluidic devices (e.g., for investigating organoids). More particularly, FIG. 1A depicts a lower material layer 14; FIG. 1B depicts an upper material layer 18 in an upside-down orientation; and FIG. 1C depicts lower and upper material layers 14, 18 coupled together in an assembled configuration.

Figure 4:
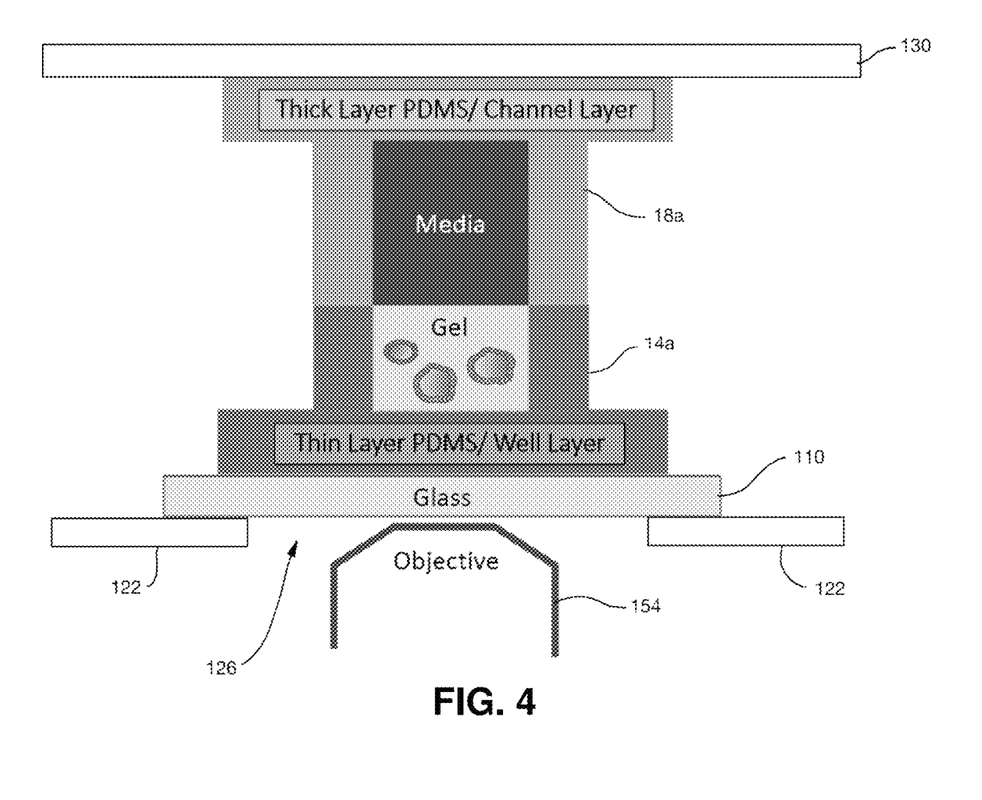
FIG. 4 depicts a conceptual cross-sectional view through a single well defined by a lower material layer in an assembled configuration with an upper material layer and the clamping assembly of FIG. 3.

The depicted example of device 10 comprises a body 22 having a first end 26, a second end 30, two lateral edges 34a and 34b, an upper side 38, and a lower side 42. Body 22 includes a first layer region 46 between a medial plane 50 and lower side 42, and a second layer region 54 between medial plane 50 and upper side 38. First layer region 46 defines one or more wells 58, for example one or more (e.g., a plurality of) rows 62 of individual wells 58, with each well 58 being open at the medial plan 50 and having a bottom between medial plane 50 and lower side 42. While first and second layer regions 46 and 54 are shown here as having similar thicknesses; in other configurations, second layer region 54 may be thicker than first layer regions (e.g., as shown in FIG. 4). Second layer region defines one or more elongated channels 66, each corresponding to at least one of the wells, for example each corresponding to a different row 62 of the wells, such that when the first and second layer regions 46, 54 (in the depicted example, lower and upper material layers 14, 18) are coupled together, each of channels 66 is aligned with one of the rows 62 of wells such that the respective elongated channel is in fluid communication with each of the wells in the respective row of wells. In the assembled configuration of FIG. 1C, fluid can be delivered to wells 58 via corresponding channels 66, for example via ports (e.g., inlets and/or outlets) through second layer region 54 (e.g., upper material layer 18) in fluid communication with the respective channel(s) 66. In the depicted example, body 22 defines ten rows 62 of eight wells 58 each, and ten corresponding channels 66. Other configurations can include different numbers of pairs of channels and rows, e.g., more than any one of, or between any two of: 10, 15, 20, 25, 30, 35, 40, 45, 50, or more.

In the depicted example, first layer region 46 is defined by lower material layer 14, and second layer region 54 is defined by upper material layer 18. Lower material layer 14 has a first surface 70 and a second surface 74 defining lower side 34 of body 22, and upper material layer 18 has a first surface 78 and a second surface 82, with first surface 78 defining upper side 38 of body 22. In the assembled configuration shown in FIG. 1C, first surface 70 of lower material layer 14 contacts second surface 82 of upper material layer 18 along medial plane 50. Thus, in the depicted example, wells 58 are open at and through first surface 70 of lower material layer 14 and extend downward (in the assembled configuration and orientation shown in FIG. 1C) toward second surface 74 to their respective bottoms between first and second surfaces 70, 74; and channels 66 are open at and through second surface 82 of upper material layer 18 and extend upward (in the assembled configuration and orientation of FIG. 1C) toward first surface 78 to their respective tops between first and second surfaces 78, 82.

While first and second layer regions 46, 54 are defined by separate material layers in the depicted example, other configurations of body 22 can be manufactured from a single material layer, for example via lithography, 3D printing, and/or the like.

Figure 2A:
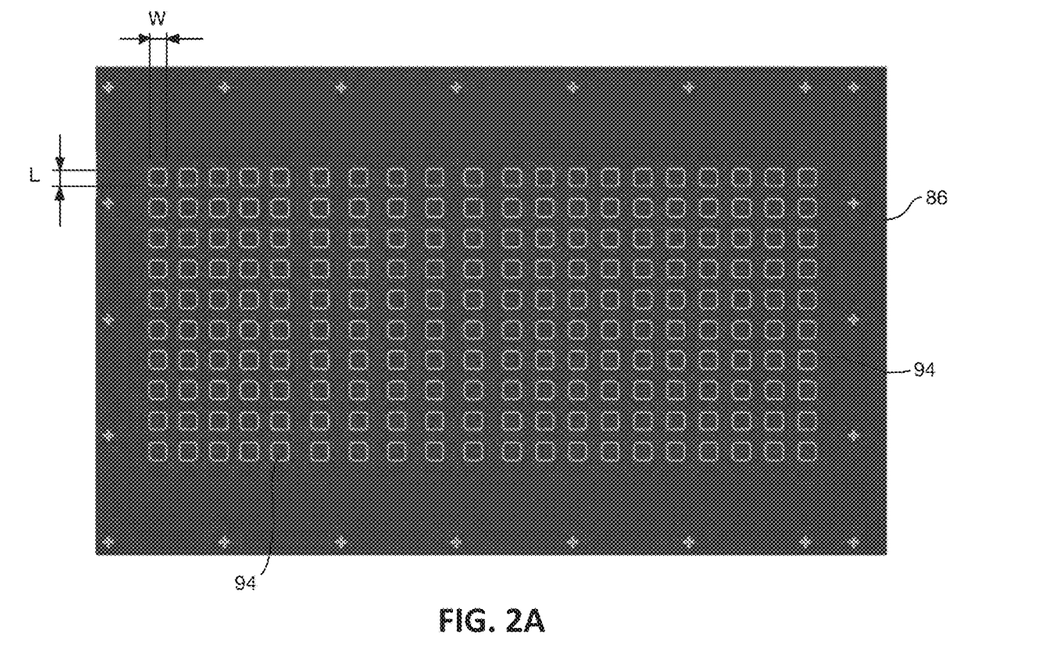
FIGS. 2A and 2B depict plan views of the design of molds (e.g., made with silicon wafers) that are configured to manufacturing with PDMS lower and upper layers, respectively, of certain examples of the present microfluidic devices.
Figure 2B:
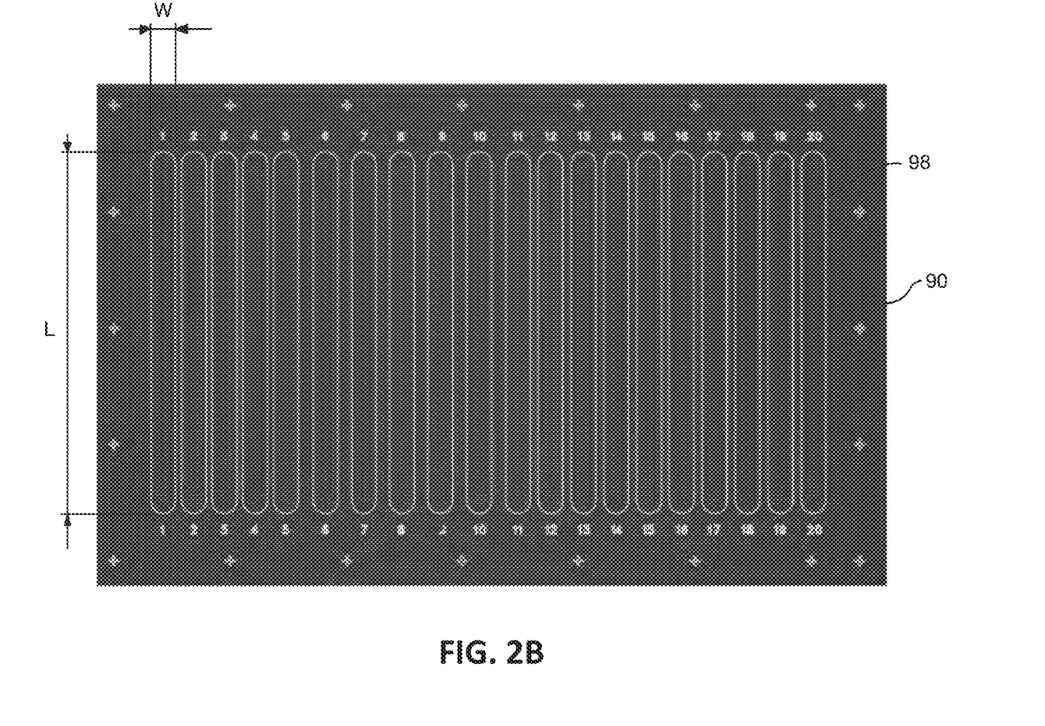

In certain configurations, such as the one shown in FIGS. 1A-1C, the body (e.g., 22) of the present devices (e.g., lower and upper material layers 14, 18) can comprise polydimethylsiloxane (PDMS). For example, upper and lower material layers can be molded from PDMS using techniques known in the art. By way of example, FIGS. 2A and 2B depict molds 86 and 90 for manufacturing the lower and upper material layers 14 and 18, respectively. In the depicted example, these molds are manufactured via photolithography on silicone-based wafers to define projections 94 on mold 86 corresponding to wells 58, and projections 98 on mold 90 corresponding to channels 66.

As shown in FIG. 2A, each of projections 94 has a width "W" corresponding to the width of a resulting well, and a length "L" in the direction of a respective row 62 corresponding to the length of the resulting well. In this configuration, the width of each projection and resulting well is substantially equal to the length; however, in other configurations, the length can be larger than (e.g., 10%, 25%, 50%, 100%, or a greater % larger than) of each projection and resulting well than the width of the projection and resulting well. For example, the width "W" and "L" may each be equal to or greater than any one of, or between any two of: 1300 µm, 1350 µm, 1400 µm, 1450 µm, 1500 µm, 1550 µm, 1600 µm, 1650 µm, and/or 1700 µm. In other configurations, each well may be circular (instead of rectangular) and may have a diameter equal to or greater than any one of, or between any two of: 1300 µm, 1350 µm, 1400 µm, 1450 µm, 1500 µm, 1550 µm, 1600 µm, 1650 µm, and/or 1700 µm. By way of example, a minimum transverse dimension of 1500 µm still permits manual pipetting of cells and/or 3D cell structures into and out of individual wells. Additionally, in this configuration, each protrusion 94 has a height extending out of the page (and each resulting well has a depth) of at least 400 micrometers (µm); for example equal to or greater than any one of, or between any two of: 400 µm, 450 µm, 500 µm, 550 µm, 600 µm, 650 µm, 700 µm, 750 µm, and/or 800 µm.

As shown in FIG. 2B, each of projections 98 has a width "W" corresponding to the width of a resulting channel, and a length "L" in the direction of a respective row 62 corresponding to the length of the resulting channel. As shown, the width of each channel can be wider (e.g., 5%, 10%, 15%, or a greater %) wider than the corresponding wells, for example to provide some tolerance for assembly and/or to ensure that fluids delivered via a channel are distributed across the entire width of a well. For example, in this configuration, each protrusion 98 has a width "W" (and each resulting channel has a width) of equal to or greater than any one of, or between any two of: 2000 µm, 2250 µm, 2500 µm, 2750 µm, 3000 µm, 3250 µm, 3500 µm; and each protrusion 98 has a length "L" (and each resulting channel has a length)

of equal to or greater than any one of, or between any two of: 25 millimeters (mm), 30 mm, 35 mm, 40 mm, 45 mm, 50 mm, and/or greater, depending for example on the number of wells in a row. Additionally, in this configuration, each protrusion 98 has a height extending out of the page (and each resulting channel has a depth) of equal to or greater than any one of, or between any two of: 300 µm, 350 µm, 400 µm, 450 µm, 500 µm, 550 µm, 600 µm.

Figure 2C:
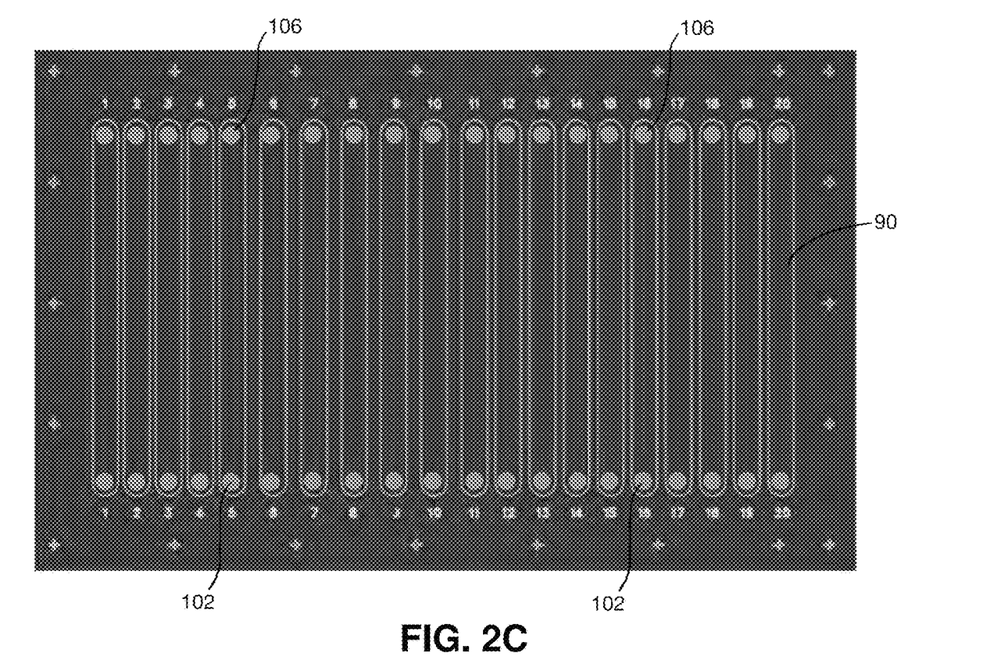
FIG. 2C depicts the upper layer design pattern of FIG. 2B with representative locations for inlets and outlets.
Figure 2D:
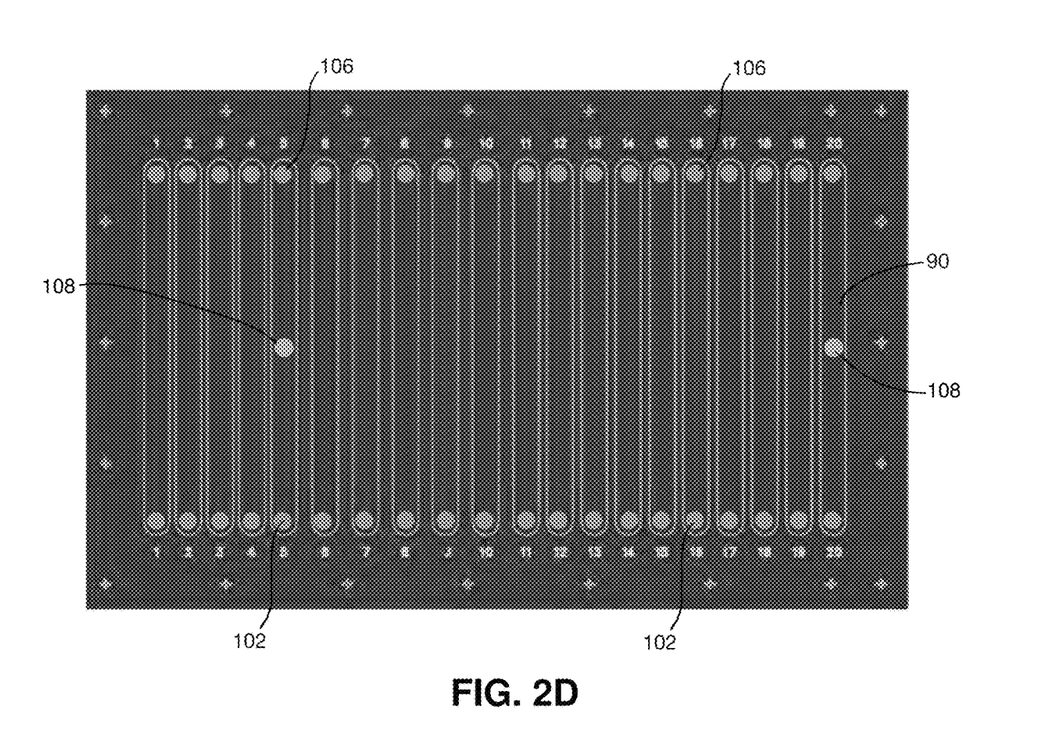
FIG. 2D depicts a variation of the upper layer design pattern of FIG. 2C that includes first, second, and third ports for at least one channel.

Thus, lower material layer 14 can be formed by pouring PDMS over mold 86, and upper material layer 18 can be formed by pouring PDMS over mold 90, and the respective layers can be baked as is known in the art. In certain configurations, body 22 can also be provided with inlets 102 (e.g., first ports) at first ends of respective channels that extend through an exterior surface of body 22 (e.g., first surface 78 of upper material layer 18), and outlets 106 (e.g., second ports) at second ends of respective channels that extend through an exterior surface of body 22 (e.g., first surface 78 of upper material layer 18), for example in the positions illustrated in FIG. 2C. Of course, body 22 can define any number of pairs of channels and rows of wells. For example, the molds depicted in FIGS. 2A-2C are configured to mold the layers of a body with twenty (20) channels and twenty (20) corresponding rows of ten (10) wells each). In some implementations, body 22 can also be provided with one or more third ports 108 positioned between the first ports and the second ports as shown in FIG. 2D, thereby enabling channels and rows of wells to be partitioned into first and second portions, such that the system can operate with different flow paths between ports. To illustrate, a first flow path between first and second ports, a second flow path between first and third ports, and a third flow path between second and third ports. In some implementations, at least one channel and row of wells may have three or more ports, such as four ports.

Figure 3:
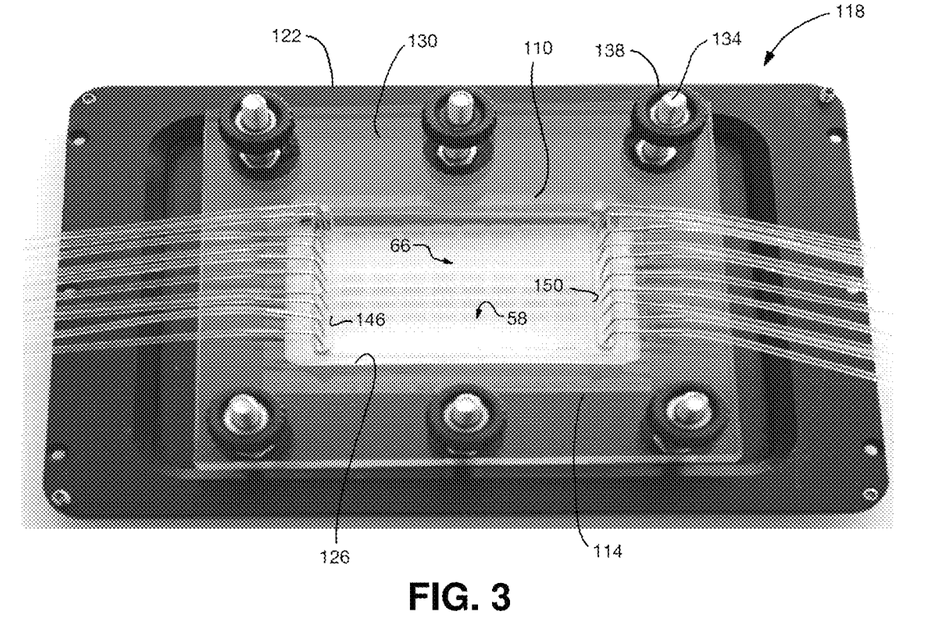
FIG. 3 depicts a perspective view of a prototype of the device of FIGS. 1A-1C in an assembled configuration with the lower and upper layers held together by a clamp assembly, and inlet and outlet conduits.

FIG. 3 depicts a prototype of body 22 of FIGS. 1A-1C. As illustrated, once or as formed, lower material layer 14 can be coupled to one or more slides, such as a first slide 110 (e.g., a 75 mm×50 mm glass slide), and upper material layer 18 can be coupled to the upper side of lower material layer 14. The slide provides a transparent, planar surface on which the material layers are supported to permit imaging of the contents of the wells. The slide may also provide structural support and rigidity to the material layers and permit the material layers to be held together by a clamp assembly 118. In the example shown, clamp assembly 118 comprises a base 122 defining an opening 126 that permits imaging of at least some (e.g., all) of wells 58 through opening 126. To permit imaging through opening 126, in this example, at least a portion of the first material layer (14) is transparent between wells 58 and first slide 110 beneath first material layer 14; alternatively, first material layer 14 can be manufactured such that first slide 110 itself defines the bottom of wells 58. In this example, clamp assembly 118 also includes an upper member 130, for example comprising a transparent polymer, that is movably coupled to the base (22) by threaded posts or screws 134 and nuts or knobs 138 that can be tightened to secure body 22 of the microfluidic device relative to base 126 (and secure upper material layer 18 relative to lower material layer 14). In the depicted example, a plurality of inlet conduits 142 extend through opening 146 in upper member 130 and through upper material layer 18 into the first ends of respective channels 66, and a plurality of outlet conduits 146 extend through opening 150 in upper member and through upper material layer 18 into the second ends of respective channels 66.

FIG. 4 depicts a conceptual cross-sectional view through a single well 58 defined by a lower material 14a in an assembled configuration with an upper material layer 18a and clamp assembly 118. While material layers 14a, 18a are simplified, conceptual versions with only a single well (or single row of wells), FIG. 4 depicts the manner in which each well can be imaged in the configuration depicted in FIG. 3. Specifically, opening 126 in base 122 permits alignment of an objective lens 154 of a microscope or other imaging device with a bottom of one or more wells such that the contents of the well(s) can be imaged through lower slide 110 (e.g., in real time during an ongoing experiment). It is noted that the phenotype of the cells as described herein mirrors that of conventional commercially available well plates. Additionally, it is noted that the fluidic structure may not disrupt and/or remove the gel from the environment, such as during flow of the media.

II. Examples of the Present Microfluidic Systems

Figure 5:
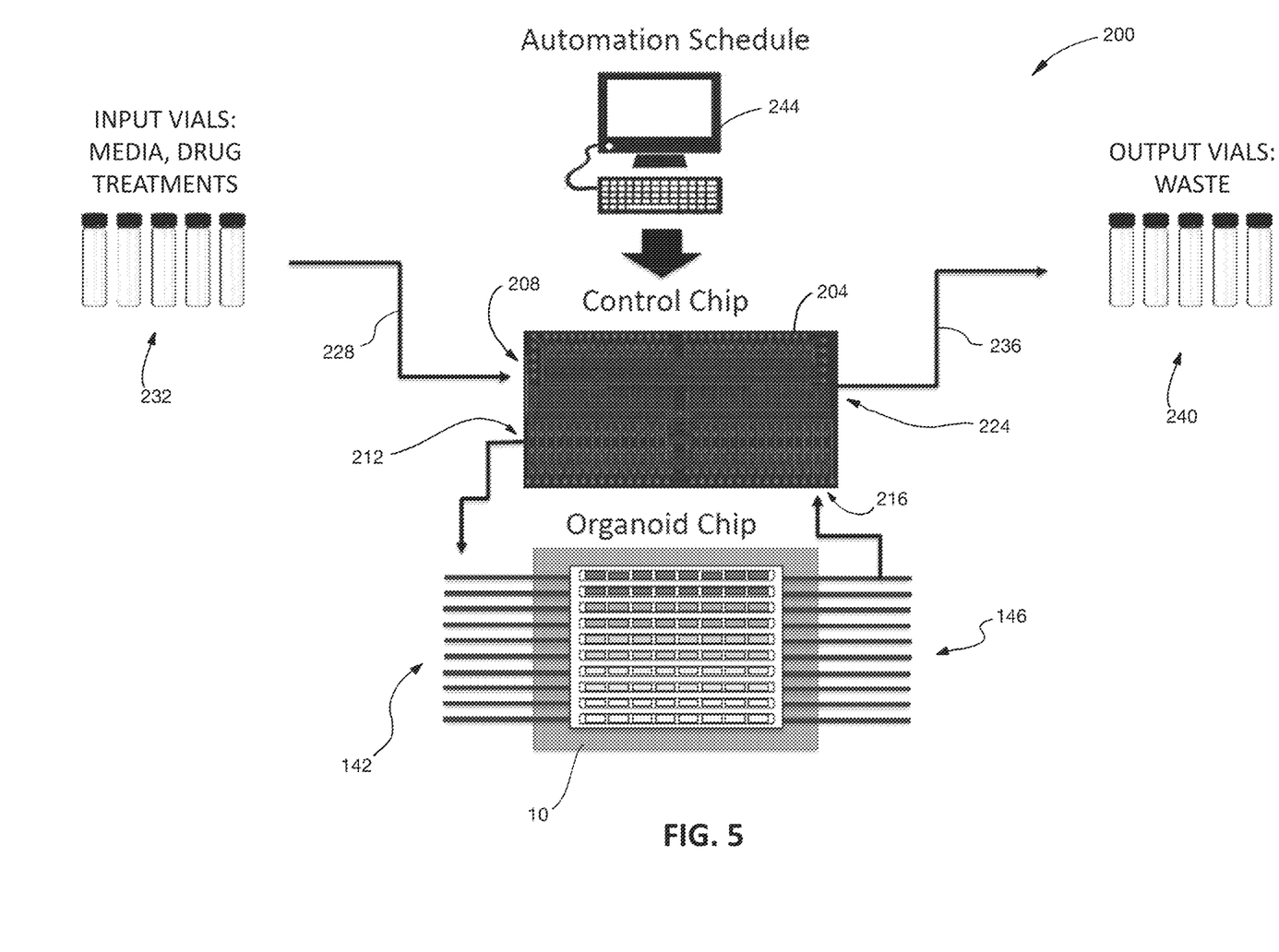
FIG. 5 depicts a schematic view of one example of the present microfluidic systems that includes the microfluidic device of FIG. 3.

FIG. 5 depicts a schematic view of an example 200 of the present microfluidic systems that includes the microfluidic device of FIG. 3. Other configurations of the present microfluidic systems can include other configurations of the present microfluidic devices. The depicted example of system 200 includes a multiplexer 204 having a plurality of multiplexer inlets 208, one or more multiplexer outlets 212, and one or more waste inlets 216. Multiplexer 204 can comprises a microfluidic multiplexer, for example also formed of PDMS, that includes a plurality of valves 220 configured to selectively permit fluid communication between respective multiplexer ports, such as multiplexer inlets 208 and multiplexer outlet(s) 212. In the depicted configuration, multiplexer outlets 212 and the waste inlet(s) 216 are in communication with corresponding ones of the elongated channels (66) of body 22 of the microfluidic device. More particularly, multiplexer outlets 212 are coupled to respective channels 66 via inlet conduits 142, and waste inlet(s) 216 is/are coupled to channels 66 via outlet conduits 146. In the depicted example, multiplexer 204 also includes one or more waste outlet(s) 224. In this example, multiplexer inlets 208 are configured to be coupled via conduits 228 to respective input reservoirs (e.g., vials) 232 with respective component fluids (e.g., growth media, drugs, and/or the like) for a given experiment. As shown, waste outlet(s) 224 is/are configured to be coupled via respective conduit(s) 236 to waste reservoirs (e.g., vials) 240 to direct waste fluids from microfluidic device 10 to the waste reservoir(s).

As will be appreciated by those of ordinary skill in the art of microfluidics, the valves (220) of multiplexer 204 are configured to selectively direct fluid from the input reservoirs (232) to one or more selected channel(s) 66 of the microfluidic device (10). The valve (220) can also be selectively opened to mix the input fluids prior to being directing to the channel(s) (66). Additionally, the valve(s) can be actuated to direct different fluids, different concentrations of fluid(s), and/or different mixtures of fluids to different ones of the channels. For example, in a device with twenty rows 62 of wells 58, organoids (e.g., organoids derived from a patient's own tumor cells) can be subjected to up to twenty different (or a control and nineteen different) drugs, drug concentrations, and/or drug combinations to determine which of the drugs, drug concentrations, or drug combinations is most effective at treating (e.g., killing) the tumor cells, for example without or with the fewest adverse effects on non-cancerous cells.

In the depicted configuration, system 200 also comprises a controller 244 coupled to microfluidic multiplexer 204 and configured to send signals to selectively open or close the valves (220) to direct flow between respective multiplexer inlets 208 and multiplexer outlet(s) 212. Controller 244 can comprise a general purpose computer with memory and a processor configured to run instructions (e.g., software) for actuating the valves (220) in a particular sequence or order for a given experimental protocol that may be predefined and/or customizable by a user, and/or that permit a user to manually direct different fluids and/or different fluid compositions to particular ones of the channel(s). Such multiplexers and software programs are generally known in the art of microfluidics; examples include: the FlowTest™ Programmable Microfluidic Controller offered by Arrayit Corporation; the Mux Wire Microfluidic Valve Controller offered by ELVESYS® Group; various microfluidics automation, flow control, and switching tools and systems (e.g., the MFCS™-EZ: Microfluidic Flow Control) offered by Fluigent, Inc.

In some implementations, example 200 may include one or more additional components, such as one or more pumps, one or more valves, and/or one or more bubble traps, as illustrative, non-limiting examples. For example, the one or more pumps may include a pressure pump (e.g., a booster pump) and/or a peristaltic pump. The one or more pumps may be coupled to or positioned to control one or more flow paths, such as flow paths via conduits (e.g., 228, 236) and/or ports (208, 212, 214, 224). The one or more valves may include valves included in multiplexer 204 or may be separate from multiplexer 204. For example, a valve may be positioned between a port and a vial, such as between port 224 and a vial 240 to enable vial 240 to be replaced with a different vial. The one or more bubble traps may be coupled to one or more conduits and/or one or more ports of example 200. The bubble trap may be configured to receive a liquid sample that includes bubbles and to output the liquid sample with a reduced amount of bubbles or that is free of bubbles. Removal of bubbles from the system may improve imaging of samples (e.g., organoids), as described herein. In a particular implementation, at least one bubble trap is positioned in fluid communication between port 212 and inlet conduit 142. At least one of the one or more additional components (e.g., a pump, a valve, a bubble trap) may be coupled to controller 244 such that operation of the at least one additional component is controlled by controller 244. For example, controller 244 may control an operational state (e.g., an on state or an off state) of a pump. In some implementations, controller 244 may control a pump to be in an on state for a particular number of operational cycles. As another example, controller 244 may be configured to operate one or more valves to keep fluid pressurized, which may prevent or remove bubbles and/or prevent backflow. In such implementations, example 200 may also include one or more pressure sensors coupled to controller 244, such as a pressure sensor coupled to port 212 and/or port 216, as an illustrative, non-limiting example, and may control one or more components, such a pump, based on a pressure detected by a pressure sensor. It is noted that when lower and upper material layers 14, 18 are coupled together in an assembled configuration, the layers 14, 18 are able to withstand fluid pressure without leaking.

In some implementations of example 200, controller 244 may control or meter fluid flow and/or a volume of fluid based on a pump cycles and/or device geometry, each of which may be specified in the case of number of pump cycles, or designed into the size of channels. Accordingly, test parameters may be controlled to enable comparative analysis between a first test sample at the system and a second, subsequent test sample at the system. Additionally, reagent additions (e.g. drug exposure times, number of drug pulses, drug combinations) may be controlled by controller 244. To illustrate, controller 244 may execute a control file to control or initiate operations of a fluidic control computer-based architecture, as described with reference to example 200. For example, controller 244 may control a temporal sequence of drugs provided from vials 232, such that different channels receive a different temporal sequence of the drugs, different durations of the drugs being provide, and/or different combinations of drugs being provided at the same time—which may produce different results (e.g., effects) in different channels. By controlling such addition with controller 244, the addition of such reagents may be performed free of human error, with improved accuracy and consistency, and accuracy of a test may depend only upon correct supply vials being connected to the system.

III. Examples of the Present Methods of Investigating 3D Cell Structures

Figure 6:
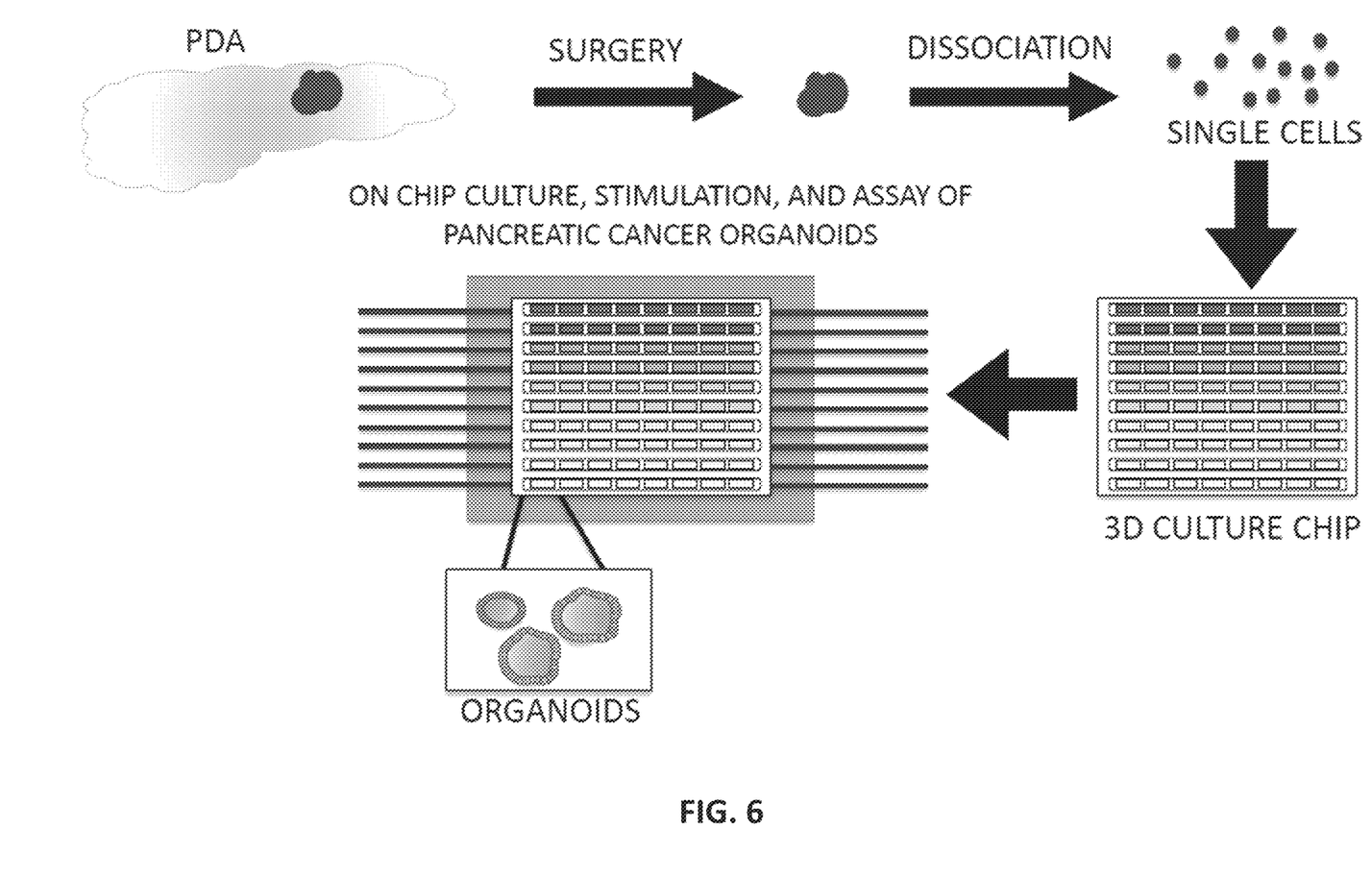
FIG. 6 depicts a flow diagram of one example of a process for obtaining cells, culturing organoids, and investigating the organoids using certain of the present microfluidic devices and systems.

FIG. 6 depicts a flow diagram of an example of a process for obtaining cells, culturing organoids, and investigating the organoids using an embodiment of the present microfluidic devices and systems. In this example, cells of pancreas ductal adenocarcinoma (PDA)—a particularly common and deadly form of pancreatic cancer—are surgically removed from a patient (e.g., via a needle or surgery), and may in some instances be dissociated into single cells or small groups of cells using techniques that are known in the art. Harvested cells can then be disposed in wells (e.g., 58) of a lower material layer 14 of one the present microfluidic devices, along with a growth media (e.g., protein gel such as Matrigel® or a hydrogel) to permit the cells to grow and form organoids, and the material layers 14, 18 of assembled as shown in FIG. 3 for culturing, stimulation, and assay of the organoids. While the depicted flowchart refers specifically to PDA, the present microfluidic devices, systems, and methods may be used to investigate various types of cancers (among other types of cells), such as, for example, breast cancers, liver cancers, gut or intestinal cancers, colon cancers, tongue and throat cancers, lung cancers, stomach cancers, prostate cancers, and/or the like. Additionally, while the flowchart contemplates seeding the wells with cells; in other instances, cells may be cultured and allowed to grow into an organoid prior to being disposed in a well of the present microfluidic devices.

Figure 7:
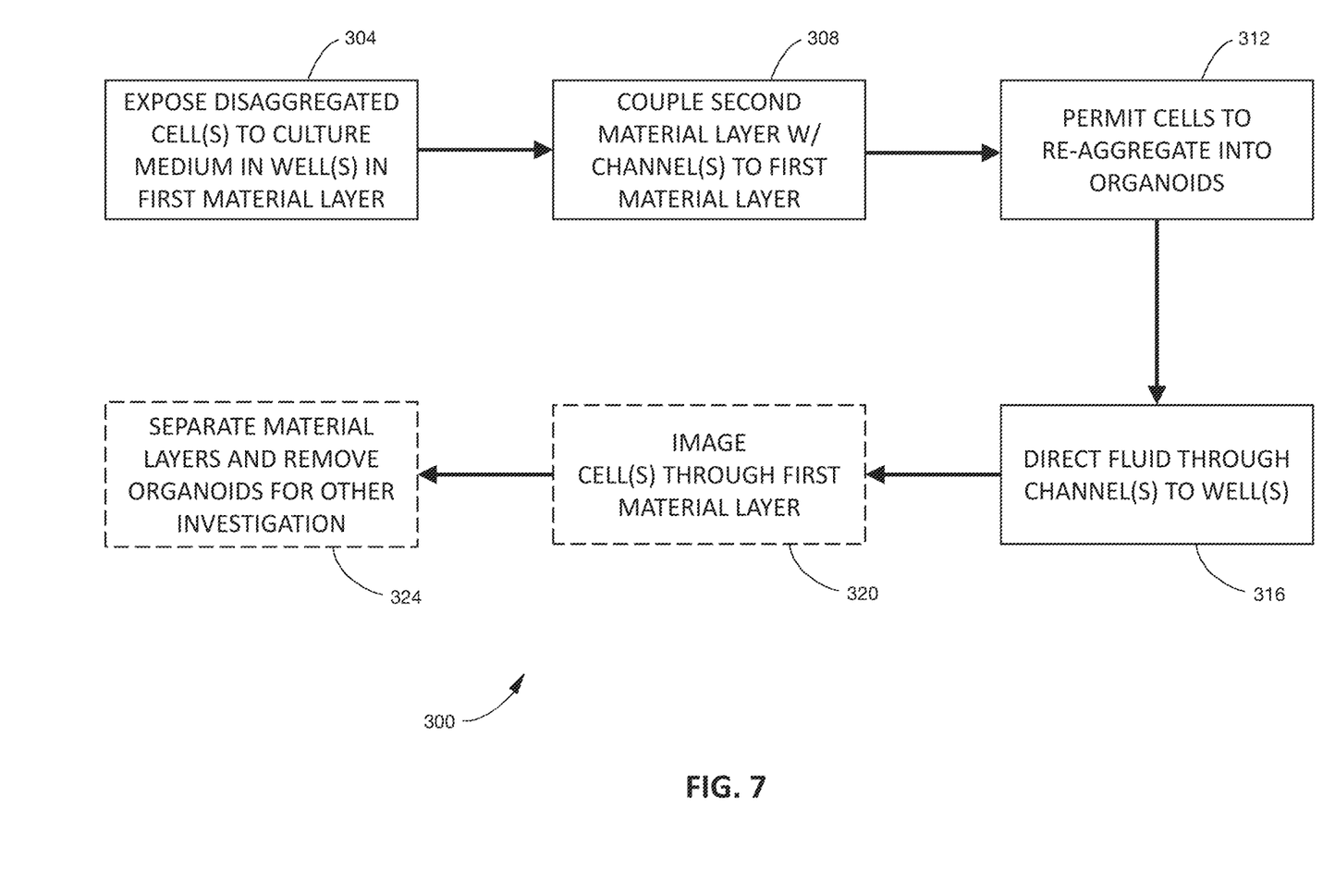
FIG. 7 depicts a flow diagram of one example of the present methods of using certain of the present microfluidic devices and systems.

FIG. 7 depicts a flow diagram of an embodiment 300 of the present methods of investigating organoids (e.g., using certain of the present microfluidic devices and systems). The depicted example includes an initial step 304 of exposing the cells to culture medium in a well (e.g., 58) of a first material layer (e.g., 14), the first material layer having a lower side (e.g., 74) and an upper side (e.g., 70) through which the well is open. The solid culture conditions in each well may include a protein gel like Matrigel® and/or a hydrogel and may, for example, substantially fill the well. The depicted example further comprises a step 308 of coupling a second material layer (e.g., 18) to the first material layer (e.g., 14) such that a lower side (e.g., 82) of the second material layer faces the upper side (e.g., 70) of the first material layer, and the second material layer is coupled to the first material layer such that the well is substantially sealed except for being in fluid communication with a channel (e.g., 66) of the second material layer. In this example, the method further comprises a step 312 of permitting the cells to form organoids, for example by culturing the cells under conditions favorable for such growth. Of course, in other implementations in which cells are matured into organoids before being disposed in a well of the present microfluidic devices, further growth may not be required after the cells are placed into the wells.

In the depicted example, the method also includes a step 316 of directing fluid (e.g., culture medium) to the well(s) of the first material layer via the channel of the second material layer. For example, the fluid can include nutrients to further encourage growth of the cells, drugs or drug combinations, stain or contrast agents, and/or any other fluids configured to assist or encourage culturing, stimulating, and/or imaging of the cells in the well. In configurations of the present microfluidic devices with a plurality of channels (e.g., 66) and corresponding wells or sets of wells, the present methods can include directing different fluid compositions (e.g., with different drugs, concentrations of drugs, and/or combinations of drugs to different channels and the corresponding wells and cells/organoids in such wells.

During and/or after the culturing and/or stimulation of the organoids, the present methods can include the optional step 320 of imaging the cells, for example through the portion of the lower or first material layer (e.g., 14) underlying the well and/or through a slide (e.g., 110) underlying the lower or first material layer).

Some implementations of the present methods can also include the optional step 324 of separating the material layers (e.g., 14 and 18) and removing one or more organoid(s) for other investigations or examinations. For example, organoid(s) can be pipetted out of the well(s) once the material layers are separated, and thereby transferred to other vessels for further expansion and/or analysis.

In addition to the examples described above, the present methods may be implemented with any configuration of the present microfluidic devices (e.g., dual or single material layer(s) and/or with 80 or 170 or 200 wells) and/or microfluidic systems (e.g., with or without a controller for automated processing), and/or with any of the steps or functions described in this disclosure (e.g., with intra-experiment staining, with stem cells instead of or in addition to cancer cells, and/or with on-chip endpoint staining of transcription factor markers for self-renewal and differentiation).

IV. Examples of Experiments with Prototypes of the Present Devices and Systems

Preliminary testing of the present microfluidic systems and methods suggest that they can offer an integrated ex vivo cancer modeling system that is superior in many ways to previously available approaches, at least in terms of ability to facilitate and accelerate preclinical cancer research, and development of personalized treatment strategies and decisions.

Figure 8A:
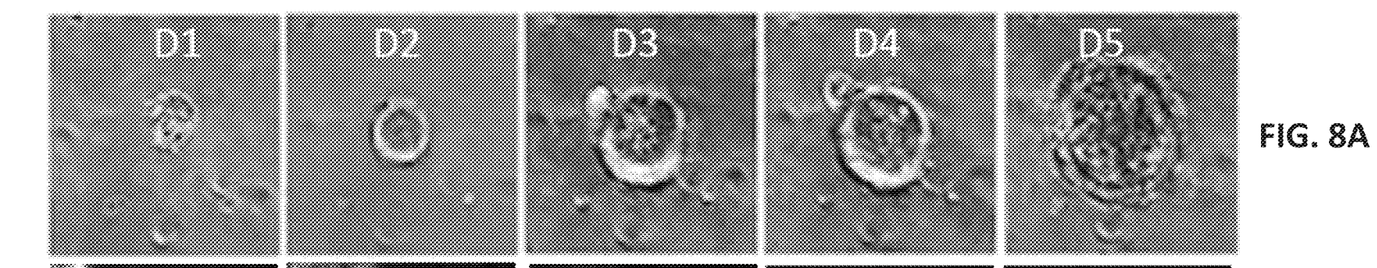
FIGS. 8A-8C depict sequences of images showing the growth of different 3D cellular structures over a five-day period (D1-D5) in a prototype of one of the present microfluidic devices.
Figure 8B:
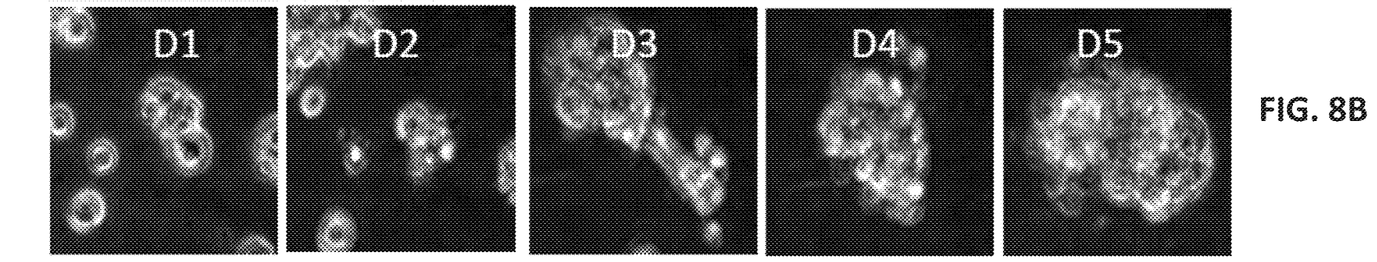
Figure 8C:
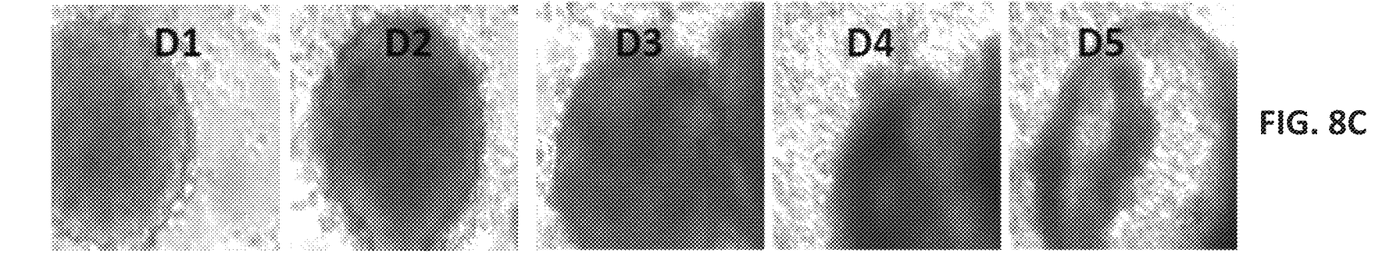

The present microfluidic systems have been used to grow a variety of three-dimensional (3D) cell structures, including pancreatic cancer organoids from patient-derived cells as shown in FIG. 8A, breast cancer cell lines (MDA-MB-231) as shown in FIG. 8B, and primary pancreatic islets from patient-derived induced mesenchymal stem cells as shown in FIG. 8C. These versatile applications of the same platform to different 3D model systems has proven a relatively easy way to culture cells under dynamic conditions for long time periods (e.g., 9+ days or even 20+ days). Additionally, the present microfluidic devices can be configured to permit continuous visual monitoring of cells during the entire culture period, and additionally permits staining for proteins during an experiment or after an experiment has been completed. Further, in certain configurations of the present microfluidic devices with removably coupled upper and lower material layers, the ability to remove an upper layer with the channels, without disturbing the underlying wells with such organoids, has proven useful in allowing subpopulations to be viably harvested via pipetting subpopulations for further expansion and analysis by simply pipetting out specific samples from desired wells identified during imaging.

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the methods and systems are not intended to be limited to the particular forms disclosed. Rather, they include all modifications and alternatives falling within the scope of the claims, and embodiments other than the one shown may include some or all of the features of the depicted embodiment. For example, elements may be omitted or combined as a unitary structure, and/or connections may be substituted. Further, where appropriate, aspects of any of the examples described above may be combined with aspects of any of the other examples described to form further examples having comparable or different properties and/or functions, and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

REFERENCES

[1] M. Junkin, A. J. Kaestli, Z. Cheng, C. Jordi, C. Albayrak, A. Hoffmann, S. Tay, "High-Content Quantification of Single-Cell Immune Dynamics," Cell Rep., vol. 15, no. 2, pp. 411-422, April 2016.
[2] R. A. Kellogg and S. Tay, "Noise Facilitates Transcriptional Control under Dynamic Inputs," Cell, vol. 160, no. 3, pp. 381-392, January 2015.
[3] M. Heltberg, R. A. Kellogg, S. Krishna, S. Tay, and M. H. Jensen, "Noise Induces Hopping between NF-κB Entrainment Modes," Cell Syst., vol. 3, no. 6, p. 532-539.e3, December 2016.
[4] L. Hutchinson and R. Kirk, "High drug attrition rates—where are we going wrong?," Nat Rev Clin Oncol, vol. 8, no. 4, pp. 189-190, April 2011.
[5] F. Pampaloni, E. G. Reynaud, and E. H. K. Stelzer, "The third dimension bridges the gap between cell culture and live tissue," Nat Rev Mol Cell Biol, vol. 8, no. 10, pp. 839-845, October 2007.
[6] L. G. Griffith and M. A. Swartz, "Capturing complex 3D tissue physiology in vitro," Nat Rev Mol Cell Biol, vol. 7, no. 3, pp. 211-224, March 2006.
[7] Ye Fang and Richard M. Eglen, "Three-Dimensional Cell Cultures in Drug Discovery and Development," SLAS Discov. 22(5): 456-472, June 2017.

The invention claimed is:
1. A microfluidic device for investigating three-dimensional (3D) cell structures, the microfluidic device comprising:
a body having a first end, a second end, two lateral edges, an upper side, a lower side, a first layer region between a medial plane of the body and the lower side, and a second layer region between the medial plane and the upper side;

where the first layer region defines one or more rows of wells, each well including an open top portion at the medial plane and a bottom between the medial plane and the lower side, and where each well has a minimum transverse dimension of 1300 microns;

where the second layer region defines one or more elongated channels that each include an open bottom portion at the medial plane and a top between the medial plane and the upper side, each elongated channel of the one or more elongated channels aligned with a respective one of the rows of wells such that the open bottom portion of each elongated channel opposes the open top portion of each well in the respective one of the rows of wells such that each elongated channel is in fluid communication with each well in the respective one of the rows of wells; and where the second layer region further defines a first port, a second port, and a third port that each extend from an exterior surface of the body and are each in fluid communication with an elongated channel of the one or more elongated channels such that a first flow path from the first port to the second port corresponds to a first set of wells of a row of wells aligned with the elongated channel and a second flow path from the second port to the third port corresponds to a second set of wells of the row of wells that is different than the first set of wells.

2. The microfluidic device of claim 1, where:

the first layer region is defined by a first material layer having a first surface and a second surface;

the second layer region is defined by a second material layer having a first surface and a second surface; and the second surface of the first material layer defines the lower side of the body;

the first surface of the second material layer defines the upper side of the body; and the first surface of the first material layer contacts the second surface of the second material layer along the medial plane.

3. The microfluidic device of claim 1, where the first layer region is coupled to a first glass slide.

4. The microfluidic device of claim 1, further comprising:

a clamp having a first frame and a second frame, the body positioned between the first and second frames, where the first frame comprises a transparent portion disposed adjacent the upper side of the second layer region; where the second frame is closer to the lower side of the body frame than the upper side of the body; and where the second frame is configured to permit imaging of at least one well through the lower side of the body; and one or more fluid conduits extending through the transparent portion and the second layer region into the one or more elongated channels such that the one or more fluid conduits are in fluid communication with the one or more elongated channels.

5. The microfluidic device of claim 1, where the first port is positioned at a first end of the elongated channel, and the third port is positioned at a second end of the elongated channel.

6. The microfluidic device of claim 1, where the upper side of the body includes the exterior surface of the body.

7. The microfluidic device of claim 1, wherein each well has a depth within a range of 400 to 800 microns, inclusive.

8. The microfluidic device of claim 1, wherein a third flow path from the first port to the third port corresponds to both the first set of wells and the second set of wells.

9. The microfluidic device of claim 1, wherein the wells of the first set of wells are distinct from the wells of the second set of wells.

10. A microfluidic device for investigating three-dimensional (3D) cell structures, the microfluidic device comprising:

a body having a first end, a second end, two lateral edges, an upper side, a lower side, a first layer region between a medial plane of the body and the lower side, and a second layer region between the medial plane and the upper side;

where the first layer region defines one or more rows of wells, each well open at the medial plane and having a bottom between the medial plane and the lower side, and where each well has a minimum transverse dimension of 1300 microns;

where the second layer region defines one or more elongated channels open at the medial plane and having a top between the medial plane and the upper side, each elongated channel of the one or more elongated channels aligned along a length of the elongated channel with a respective one of the rows of wells such that the elongated channel is in fluid communication with each well in the respective one of the row of wells, and where the elongated channel has a width greater than the minimum transverse dimension of each well in the respective one of the row of wells; and where the second layer region further defines a first port, a second port, and a third port that each extend from an exterior surface of the body and are each in fluid communication with an elongated channel of the one or more elongated channels such that a first flow path from the first port to the second port corresponds to a first set of wells of a row of wells aligned with the elongated channel and a second flow path from the second port to the third port corresponds to a second set of wells of the row of wells that is different than the first set of wells.

11. The microfluidic device of claim 10, where each well includes an open top portion, each elongated channel includes an open bottom portion, and the open bottom portion of each elongated channel opposes the open top portion of each well in the respective one of the rows of wells.

12. The microfluidic device of claim 10, wherein a plane perpendicular to both the medial plane and an elongated channel of the one or more elongated channels extends through a well of the one or more rows of wells and the elongated channel.

* * * * *